US007829723B2

(12) United States Patent
Blythe et al.

(10) Patent No.: US 7,829,723 B2
(45) Date of Patent: *Nov. 9, 2010

(54) POLYMORPHIC FORMS OF (S)-1-CYANOBUTAN-2-YL (S)-1-(3-3-(3-METHOXY-4-(OXAZOL-5-YL) PHENYL)URIEDO)PHENYL)ETHYL CARBAMATE

(75) Inventors: Todd Blythe, Georgetown, MA (US); Petinka Vlahova, West Lafayette, IN (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/365,424

(22) Filed: Feb. 4, 2009

(65) Prior Publication Data
US 2009/0170915 A1    Jul. 2, 2009

Related U.S. Application Data

(62) Division of application No. 11/440,891, filed on May 25, 2006, now Pat. No. 7,504,515.

(60) Provisional application No. 60/684,644, filed on May 27, 2005.

(51) Int. Cl.
*C07D 263/32* (2006.01)

(52) U.S. Cl. ..................................................... 548/236
(58) Field of Classification Search .................. 548/236
See application file for complete search history.

(56) References Cited

U.S. PATENT DOCUMENTS 6,498,178 B2 * 12/2002 Stamos et al. ............... 514/374
7,504,515 B2    3/2009 Blythe et al.
2002/0111378 A1    8/2002 Stamos et al.

FOREIGN PATENT DOCUMENTS

WO    2004/052349    6/2004

OTHER PUBLICATIONS

Byrn, et al., ed. "Comparing X-ray Powder Data". Solid State Chemistry of Drugs, $2^{nd}$ edition, p. 63, (1999)*
A. Maureen Rouhi, Chemical & Engineering News, Feb. 24, 2003, pp. 32-35.*
Haleblian, et al. Journal of Pharmaceutical Sciences, Aug. 1969, vol. 58, No. 8, pp. 911-929.*

* cited by examiner

*Primary Examiner*—Rebecca L Anderson
*Assistant Examiner*—Shawquia Young
(74) *Attorney, Agent, or Firm*—Michael C. Badia

(57) ABSTRACT

The present invention relates to polymorphic forms of (S)-1-cyanobutan-2-yl (S)-1-(3-(3-(3-methoxy-4-(oxazol-5-yl) phenyl)ureido)phenyl)ethylcarbamate, pharmaceutical compositions thereof, processes to prepare therein, and uses therewith.

10 Claims, 5 Drawing Sheets

POLYMORPHIC FORMS OF (S)-1-CYANOBUTAN-2-YL (S)-1-(3-3-(3-METHOXY-4-(OXAZOL-5-YL) PHENYL)URIEDO)PHENYL)ETHYL CARBAMATE

CROSS REFERENCE TO RELATED APPLICATIONS

This application is a divisional of U.S. patent application Ser. No. 11/440,891, filed May 25, 2006, now U.S. Pat. No. 7,504,515 which claims the benefit under 35 U.S.C. §119(e) of U.S. provisional application Ser. No. 60/684,644, filed May 27, 2005, the entire contents of each application being incorporated herein by reference.

TECHNICAL FIELD OF THE INVENTION

The present invention relates to polymorphic forms of (S)-1-cyanobutan-2-yl (S)-1-(3-(3-(3-methoxy-4-(oxazol-5-yl)phenyl)ureido)phenyl)ethylcarbamate, processes therein, pharmaceutical compositions thereof, and methods therewith.

BACKGROUND OF THE INVENTION

The present invention relates to polymorphic forms of (S)-1-cyanobutan-2-yl (S)-1-(3-(3-(3-methoxy-4-(oxazol-5-yl)phenyl)ureido)phenyl)ethylcarbamate having the structure below (hereinafter "Compound 1"):

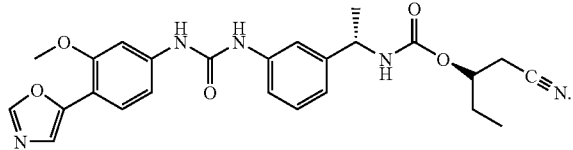

The present invention also relates to processes to prepare polymorphic forms of Compound 1.

Compound 1 is a potent IMPDH inhibitor useful in treating IMPDH-mediated diseases. Compound 1, compositions thereof, and methods therewith are disclosed in U.S. Pat. No. 6,498,178 ((hereinafter "the '178 patent"), the entire disclosure whereof is incorporated herein by reference

SUMMARY OF THE INVENTION

The present invention provides two polymorphic forms of Compound 1, namely, Form A1 and Form B2. The present invention also relates to processes for making these polymorphic forms. The invention also relates to the use of these polymorphic forms in therapeutic methods and in the preparation of pharmaceutical compositions comprising such polymorphic forms. The present invention also relates to an amorphous form of Compound 1 and processes for producing such an amorphous form.

Figure 1:
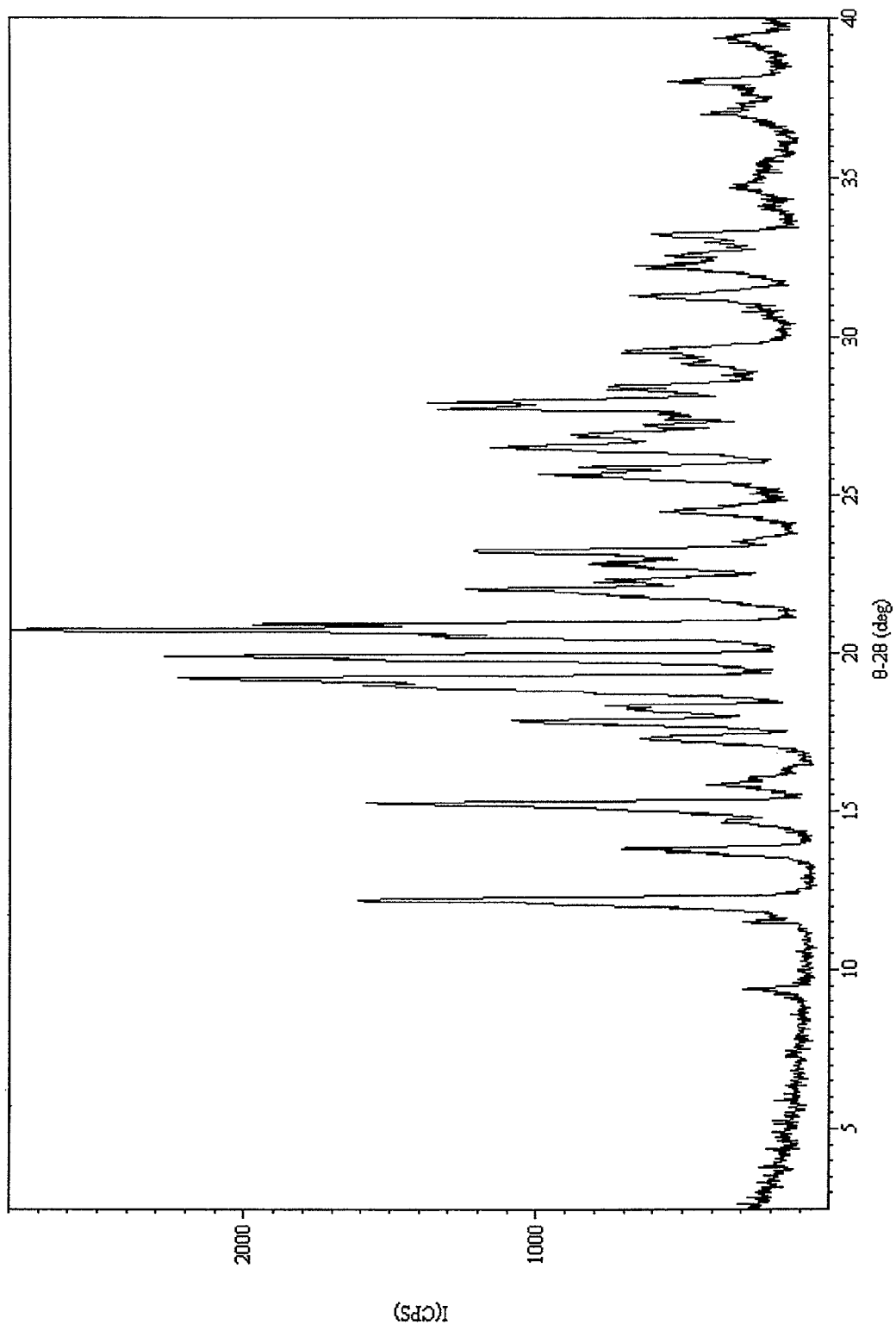
FIG. 1 is an x-ray powder diffraction pattern (XRPD) of Form A1 of (S)-1-cyanobutan-2-yl (S)-1-(3-(3-(3-methoxy-4-(oxazol-5-yl)phenyl)ureido)phenyl)ethylcarbamate.

DETAILED DESCRIPTION OF THE INVENTION (S)-1-cyanobutan-2-yl (S)-1-(3-(3-(3-methoxy-4-(oxazol-5-yl)phenyl)ureido)phenyl)ethylcarbamate (Compound 1) is a potent IMPDH inhibitor useful in treating IMPDH-mediated diseases. Two polymorphic forms of the free base of Compound 1 (Form A1 and Form B2) have been identified.

The polymorphs of the present invention may occur as racemates, racemic mixtures, and diastereomeric mixtures with all possible isomers and mixtures thereof being included in the present invention.

According to one embodiment, the present invention provides polymorphic Form A1 and Form B2 of Compound 1 with the (S) stereochemistry as indicated in the structure of Compound 1 herein.

According to one embodiment, the present invention provides a polymorphic Form A1 of (S)-1-cyanobutan-2-yl (S)-1-(3-(3-(3-methoxy-4-(oxazol-5-yl)phenyl)ureido)phenyl) ethylcarbamate.

According to another embodiment, the present invention provides a substantially pure polymorphic Form A1 of (S)-1-cyanobutan-2-yl (S)-1-(3-(3-(3-methoxy-4-(oxazol-5-yl)phenyl)ureido)phenyl)ethylcarbamate, wherein said polymorph comprises less than about 5% by weight of amorphous form.

According to another embodiment, the present invention provides a substantially pure polymorphic Form A1 of (S)-1-cyanobutan-2-yl (S)-1-(3-(3-(3-methoxy-4-(oxazol-5-yl)phenyl)ureido)phenyl)ethylcarbamate, wherein said polymorph comprises less than about 4% by weight of amorphous form.

According to another embodiment, the present invention provides a substantially pure polymorphic Form A1 of (S)-1-cyanobutan-2-yl (S)-1-(3-(3-(3-methoxy-4-(oxazol-5-yl)phenyl)ureido)phenyl)ethylcarbamate, wherein said polymorph comprises less than about 3% by weight of amorphous form.

According to another embodiment, the present invention provides a substantially pure polymorphic Form A1 of (S)-1-cyanobutan-2-yl (S)-1-(3-(3-(3-methoxy-4-(oxazol-5-yl)phenyl)ureido)phenyl)ethylcarbamate, wherein said polymorph comprises less than about 5% by weight of either amorphous form or Form B2.

According to another embodiment, the present invention provides a polymorphic Form A1 of Compound 1 wherein the polymorph has a peak position at about 20.7 degrees 2-theta in an x-ray powder diffraction pattern obtained using Cu K alpha radiation.

According to another embodiment, the present invention provides a polymorphic Form A1 of Compound 1 wherein the polymorph has at least one additional peak position at about 12.2, 15.2, 19.8, or 23.2 degrees 2-theta in an x-ray powder diffraction pattern obtained using Cu K alpha radiation.

According to another embodiment, the present invention provides a polymorphic Form A1 of Compound 1 wherein the polymorph exhibits an endothermic event between about 160° C. and about 176° C. measured by a Differential Scanning Calorimeter (DSC). Depending on the rate of heating or the scan rate at which the DSC analysis is conducted, the calibration standard used, the relative humidity and upon the chemical purity, the endotherms of the respective Forms A1, B2, and amorphous form may vary by about 0.01 to 100° C. above or below the endotherms depicted in the Figures. For any given sample, the observed endotherm may also differ from instrument to instrument; however, it will generally be within the ranges defined herein provided the instruments are calibrated similarly.

According to another embodiment, the present invention provides a process for preparing Form A1, as exemplified herein below.

According to another embodiment, the present invention provides a method of converting polymorph Form B2 to Form A1 by spontaneous crystallization of Form B2 in methanol or acetone to give Form A1.

According to another embodiment, the present invention provides a process for preparing substantially pure polymorphic Form A1 of (S)-1-cyanobutan-2-yl (S)-1-(3-(3-(3-methoxy-4-(oxazol-5-yl)phenyl)ureido)phenyl)ethylcarbamate comprising slow evaporation, fast evaporation, slow cool, crash cool, vapor diffusion, or slurry, or combinations thereof in a suitable solvent or mixtures of suitable solvents.

In one embodiment, substantially pure polymorphic Form A1 is prepared by slow evaporation in acetone.

In another embodiment, substantially pure polymorphic Form A1 is prepared by fast evaporation in a mixture of about toluene-tetrahydrofuran.

In another embodiment, substantially pure polymorphic Form A1 is prepared by slow cool in acetone.

In another embodiment, substantially pure polymorphic Form A1 is prepared by a crash cool in acetone or methanol.

In another embodiment, substantially pure polymorphic Form A1 is prepared by vapor diffusion in methanol and water.

In another embodiment, substantially pure polymorphic Form A1 is prepared by a slurry in methanol, methyl t-butyl ether, or toluene or a mixture of acetone and water.

In another embodiment, substantially pure polymorphic Form A1 is prepared by slow cool and fast evaporation in acetone.

In another embodiment, substantially pure polymorphic Form A1 is prepared by

According to another embodiment, the present invention provides a pharmaceutical composition comprising Form A1 and a pharmaceutically acceptable carrier or adjuvant.

According to another embodiment, the present invention provides a method of formulating a pharmaceutical composition comprising Form A1 of Compound 1, comprising the step of combining said Form A1 with one or more suitable pharmaceutical carrier or adjuvant.

According to another embodiment, the present invention provides a method of treating an IMPDH-mediated disease in a patient comprising the step of administering to said patient a therapeutically effective amount of substantially pure Form A1 or a pharmaceutical composition comprising substantially pure Form A1.

According to another embodiment, the present invention provides a process for preparing a substantially pure polymorph of Form A1, said process comprising at least one of the following steps:

a) dissolving (S)-1-cyanobutan-2-yl (S)-1-(3-(3-(3-methoxy-4-(oxazol-5-yl)phenyl)ureido)phenyl)ethylcarbamate in a suitable solvent with suitable agitation at a suitable temperature to give a suitable solution;

b) cooling said solution to about room temperature to give a suspension;

c) filtering or centrifuging said suspension to give polymorph Form A1;

d) rinsing said Form A1 a suitable number of times with a suitable solvent; and e) drying said Form A1 at a suitable temperature under a suitable reduced pressure for a suitable period of time to constant weight.

According to another embodiment, suitable solvents for step a) include those listed in Table 1 herein below.

According to another embodiment, the present invention provides a polymorphic Form B2 of (S)-1-cyanobutan-2-yl (S)-1-(3-(3-(3-methoxy-4-(oxazol-5-yl)phenyl)ureido)phenyl)ethylcarbamate.

According to another embodiment, the present invention provides a polymorphic Form B2 wherein the polymorph has a peak position at about 4.1 degrees 2-theta in an x-ray powder diffraction pattern obtained using Cu K alpha radiation.

According to another embodiment, the present invention provides a polymorphic Form B2 wherein the polymorph has at least one additional peak position at about 12.6, 14.4, 16.4, 22.1, or 27.1 degrees 2-theta in an x-ray powder diffraction pattern obtained using Cu K alpha radiation.

According to another embodiment, the present invention provides a process for preparing Form B2, as exemplified herein below.

According to another embodiment, the present invention provides a pharmaceutical composition comprising Form B2 and a pharmaceutically acceptable carrier or adjuvant.

According to another embodiment, the present invention provides a method of formulating a pharmaceutical composition comprising an amorphous form of Compound 1, comprising the steps of:

(i) converting Form A1 to an amorphous form; and (ii) combining said amorphous form with one or more suitable pharmaceutical carrier or adjuvant.

According to another embodiment, the present invention provides a method of treating an IMPDH-mediated disease in a patient comprising the step of administering to said patient a therapeutically effective amount of Form B2 or a pharmaceutical composition comprising Form B2.

According to another embodiment, the present invention provides a substantially pure amorphous form of (S)-1-cyanobutan-2-yl (S)-1-(3-(3-(3-methoxy-4-(oxazol-5-yl)phenyl)ureido)phenyl)ethylcarbamate wherein said amorphous form comprises less than 5% by weight of Form A1.

According to another embodiment, the present invention provides an amorphous form of (S)-1-cyanobutan-2-yl (S)-1-(3-(3-(3-methoxy-4-(oxazol-5-yl)phenyl)ureido)phenyl)ethylcarbamate.

According to another embodiment, the present invention provides an amorphous form wherein the amorphous form exhibits an endothermic event at about 168° C. and a broad endothermic event at about 214° C. as measured by a Differential Scanning Calorimeter.

According to another embodiment, the present invention provides a process to prepare an amorphous form of (S)-1-cyanobutan-2-yl (S)-1-(3-(3-(3-methoxy-4-(oxazol-5-yl)phenyl)ureido)phenyl)ethylcarbamate comprising slow cool, slow evaporation, crash cool, or fast evaporation or combinations thereof of a solution of polymorphic Form A1 in a suitable solvent or mixtures of suitable solvents.

In another embodiment, the amorphous form is prepared by slow evaporation in 2-butanone.

In another embodiment, the amorphous form is prepared by fast evaporation in absolute ethanol or a mixture of acetonitrile and n-propanol.

In another embodiment, the amorphous form is prepared by slow cool and fast evaporation in methanol.

In another embodiment, the amorphous form is prepared by crash cool and fast evaporation in tetrahydrofuran.

According to another embodiment, the present invention provides a pharmaceutical composition comprising the amorphous form according to any of the embodiments herein, wherein said composition is produced by combining said amorphous form with one or more suitable pharmaceutical carriers or adjuvants.

According to another embodiment, the present invention provides a pharmaceutical composition comprising an amorphous form of Compound 1 and a pharmaceutical acceptable adjuvant or carrier.

According to another embodiment, the present invention provides a method of treating an IMPDH-mediated disease in a patient comprising the step of administering to said patient a therapeutically effective amount of amorphous form or a pharmaceutical composition comprising amorphous form.

The term "suitable" as used herein, describes solvent, temperature, filtrate, agitation, solution, medium, quantity, period of time, etc. Such suitable solvents, temperature, filtrate, agitation, solution, medium, quantity, period of time, etc. are readily known to one of skill in the art.

The term "pharmaceutically acceptable carrier or adjuvant" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4} \text{alkyl})_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In one embodiment, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

When the compositions of this invention comprise a combination of an IMPDH inhibitor of this invention and one or more additional therapeutic or prophylactic agents, such as those disclosed herein, both the IMPDH inhibitor and the additional agent(s) should be present at dosage levels of between about 10 to 100%, and more preferably between about 10 to 80% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

When the compositions of this invention comprise a combination of an IMPDH inhibitor of this invention and one or more additional therapeutic or prophylactic agents, both the compound and the additional agent should be present at dosage levels of between about 10 to 100% and in another embodiment between about 10 to 80% of the dosage normally administered in a monotherapy regimen.

According to one embodiment, the pharmaceutical compositions of this invention comprise an additional immunosuppression agent. Examples of additional immunosuppression agents include, but are not limited to, cyclosporin A, FK506, rapamycin, leflunomide, deoxyspergualin, prednisone, azathioprine, mycophenolate mofetil, OKT3, ATAG, mizoribine, and interferon including alpha-interferon such as PEG-Intron® and Pegasys®.

The term "interferon" as used herein means a member of a family of highly homologous species-specific proteins that inhibit viral replication and cellular proliferation, and modulate immune response, such as interferon alpha, interferon beta, or interferon gamma. The Merck Index, entry 5015, Twelfth Edition.

According to one embodiment of the present invention, the interferon is α-interferon. According to another embodiment, a therapeutic combination of the present invention utilizes natural alpha interferon 2a. Or, the therapeutic combination of the present invention utilizes natural alpha interferon 2b. In another embodiment, the therapeutic combination of the present invention utilizes recombinant alpha interferon 2a or 2b. In yet another embodiment, the interferon is pegylated alpha interferon 2a or 2b. Interferons suitable for the present invention include:
(a) Intron (interferon-alpha 2B, Schering Plough),
(b) Peg-Intron,
(c) Pegasys,
  (d) Roferon,
  (e) Berofor,
  (f) Sumiferon,
  (g) Wellferon,
(h) consensus alpha interferon available from Amgen, Inc., Newbury Park, Calif.,
  (i) Alferon;
    (j) Viraferon®;
    (k) Infergen®.

According to an alternate embodiment, the pharmaceutical compositions of this invention may additionally comprise an anti-cancer agent. Examples of anti-cancer agents include, but are not limited to, cis-platin, actinomycin D, doxorubicin, vincristine, vinblastine, etoposide, amsacrine, mitoxantrone, tenipaside, taxol, colchicine, cyclosporin A, phenothiazines, interferon and thioxantheres.

In another embodiment, the compositions of this invention additionally comprise another anti-viral agent, including an anti-HCV agent. Such anti-viral agents include, but are not limited to, immunomodulatory agents, such as α-, β-, and γ-interferons, pegylated derivatized interferon-α compounds, and thymosin; other anti-viral agents, such as ribavirin (and the combination therapy of ribavirin and pegylated interferon [Rebetrol®]), d4T, ddI, AZT, amprenavir, fos-amprenavir, acyclovir, NS3-NS4A protease inhibitors such as those disclosed in PCT publication No. WO 02/018369, amantadine, cytovene, ganciclovir, ritonivir, trisodium phosphonoformate, and telbivudine; other inhibitors of hepatitis C proteases (NS2-NS3 inhibitors and NS3-NS4A inhibitors); inhibitors of other targets in the HCV life cycle, including but not limited to, helicase and polymerase inhibitors; inhibitors of internal ribosome entry; and broad-spectrum viral inhibitors, such as IMPDH inhibitors (e.g., IMPDH inhibitors disclosed in U.S. Pat. Nos. 5,807,876 and 6,498,178, mycophenolic acid and derivatives thereof).

In one embodiment, the compositions of this invention additionally comprise another agent, including a cytochrome P-450 inhibitor. Such cytochrome P-450 inhibitors include, but are not limited to, ritonavir. CYP inhibitors may be useful in increasing liver concentrations and/or increasing blood levels of compounds that are inhibited by CYP.

If an embodiment of this invention involves a CYP inhibitor, any CYP inhibitor that improves the pharmacokinetics of the IMPDH inhibitor may be used in a method of this invention. These CYP inhibitors include, but are not limited to, ritonavir (WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole. For preferred dosage forms of ritonavir, see U.S. Pat. No. 6,037,157, and the documents cited therein: U.S. Pat. No. 5,484,801, U.S. application Ser. No. 08/402,690, and International Applications WO 95/07696 and WO 95/09614).

Methods for measuring the ability of a compound to inhibit cytochrome P450 monooxygenase activity are known (see U.S. Pat. No. 6,037,157 and Yun, et al. *Drug Metabolism & Disposition, vol.* 21, pp. 403-407 (1993).

According to yet another alternate embodiment, the pharmaceutical compositions of this invention may additionally comprise an anti-vascular hyperproliferative agent. Examples of anti-vascular hyperproliferative agents include, but are not limited to, HMG Co-A reductase inhibitors such as lovastatin, thromboxane A2 synthetase inhibitors, eicosapentanoic acid, ciprostene, trapidil, ACE inhibitors, low molecular weight heparin, mycophenolic acid, rapamycin and 5-(3'-pyridinylmethyl)benzofuran-2-carboxylate.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

According to one embodiment, the term "IMPDH-mediated disease" as used herein includes immune system related diseases such as transplant rejection (e.g., kidney, liver, heart, lung, pancreas (islet cells), bone marrow, cornea, small bowel and skin allografts and heart valve xenografts), graft versus host disease, and autoimmune diseases, such as rheumatoid arthritis, multiple sclerosis, juvenile diabetes, asthma, inflammatory bowel disease (Crohn's disease, ulcerative colitis), lupus, diabetes, mellitus myasthenia gravis, psoriasis, dermatitis, eczema, seborrhea, pulmonary inflammation, eye uveitis, Grave's disease, Hashimoto's thyroiditis, Behcet's or Sjorgen's syndrome (dry eyes/mouth), pernicious or immunohaemolytic anaemia, idiopathic adrenal insufficiency, polyglandular autoimmune syndrome, glomerulonephritis, scleroderma, lichen planus, viteligo (depigmentation of the skin), autoimmune thyroiditis, and alveolitis.

According to another embodiment, the term "IMPDH-mediated disease" as used herein includes viral diseases such as DNA and RNA viral diseases caused by infection for example, by orthomyxoviruses (influenza viruses types A and B), paramyxoviruses (respiratory syncytial virus (RSV), subacute sclerosing panencephalitis (SSPE) virus) measles and parainfluenza type 3), herpesviruses (HSV-1, HSV-2, HHV-6, HHV-7, HHV-8, Epstein Barr Virus (EBV), cytomegalovirus (HCMV) and varicella zoster virus (VZV)), retroviruses (HIV-1, HIV-2, HTLV-1, HTLV-2), flavi- and pestiviruses (yellow fever virus (YFV), hepatitis C virus (HCV), dengue fever virus, bovine viral diarrhea virus (BVDV), hepatotrophic viruses (hepatitis A virus (HAV), hepatitis B virus (HBV), hepatitis D virus (HDV), hepatitis E virus (HEV), hepatitis G virus (HGV), Crimean-Congo hemorrhagic fever virus (CCHF), bunyaviruses (Punta Toro virus, Rift Valley fever virus (RVFV), and sandfly fever Sicilian virus), Hantaan virus, Caraparu virus), human papilloma viruses, encephalitis viruses (La Crosse virus), arena viruses (Junin and Tacaribe virus), reovirus, vesicular stomatitis virus, rhinoviruses, enteroviruses (polio virus, coxsackie viruses, encephalomyocarditis virus (EMC)), Lassa fever virus, and togaviruses (Sindbis and Semlike forest viruses) and poxviruses (vaccinia virus), adenoviruses, rubiola, and rubella.

According to another embodiment, the term "IMPDH-mediated disease" as used herein includes vascular cellular hyperproliferative diseases such as restenosis, stenosis, artherosclerosis and other hyperproliferative vascular disease.

According to another embodiment, the term "IMPDH-mediated disease" as used herein includes tumors and malignancies, such as lymphoma, leukemia and other forms of cancer such as breast cancer, prostate cancer, colon cancer, pancreatic cancer, etc.

According to another embodiment, the term "IMPDH-mediated disease" as used herein includes inflammatory diseases such as osteoarthritis, acute pancreatitis, chronic pancreatitis, asthma and adult respiratory distress syndrome.

Suitable methods for the conversion of a crystalline form, such as a polymorphic form of the present invention, into an amorphous form suitable for formulation are well known in the art. See, e.g., "Remington: The Science & Practice of Pharmacy"; Alfonso R. Gennaro, Editor, Mack Publishing, 1995, 19th Edition, Volume 2, the entire disclosure whereof is incorporated herein by reference.

In order that the invention described herein may be more fully understood, the following experimental methods, assays, and examples are set forth. The following experimental methods, assays, and examples are offered by way of illustration, not limitation.

Experimental Methods

X-RAY Powder Diffraction (XRPD)

XRPD analyses were carried out on a Shimadzu XRD-6000 X-ray powder diffractometer using Cu K$\alpha$ radiation. The instrument is equipped with a fine focus X-ray tube. The tube power and amperage were set at 40 kV and 40 mA, respectively. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2.5 to 40° 2$\theta$ was used. A silicon standard was analyzed each day to check the instrument alignment. Samples were packed in aluminum holder with either silicon well or silicon insert.

Differential Scanning Calorimetry (DSC)

Differential scanning calorimetry data was collected on a TA Instruments differential scanning calorimeter 2920. Each sample was heated under nitrogen at a rate of 10° C./min, up to a final temperature of 250 or 350° C. Indium metal was used as the calibration standard. Reported DSC temperatures are at the transition maxima. Approximately 2-5 mg of sample was placed into a DSC pan, and the weight accurately recorded. The pan was hermetically sealed with a lid containing a laser pinhole to allow for pressure release.

Thermogravimetric Analysis (TGA)

Thermogravimetric (TG) analyses were carried out on a TA Instruments 2050 or 2950 thermogravimetric analyzer. The calibration standards were nickel and Alumel™. Approximately 5-25 mg of sample were placed in the pan, inserted into the TG furnace, and accurately weighed. The samples were heated in nitrogen at a rate of 10° C./min, up to a final temperature of 250° C.

For studies of the glass transition temperature ($T_g$) of the amorphous material, the sample was heated under nitrogen at a rate of 20° C./min up to 100° C. The sample was held at this temperature for 1 minute and then allowed to cool and equilibrate at 0° C. After an isothermal hold for 5 minutes, the sample was again heated at a rate of 20° C./min through the same cycle for a second time. The sample was then heated at 20° C./min up to a final temperature of 200 or 250° C.

Thermogravimetric Infrared (TG/IR)

Thermogravimetric infrared (TG/IR) analyses were acquired on a TA Instruments thermogravimetric analyzer (TG) model 2050 interfaced to a Magna 560® Fourier transform infrared (FT-IR) spectrophotometer (Nicolet Instrument Corp.) equipped with an Ever-Glo mid/far IR source, a potassium bromide (KBr) beamsplitter, and a deuterated triglycine sulfate (DTGS) detector. Each IR spectrum represents 8 co-added scans acquired at a spectral resolution of 4 $cm^{-1}$. IR spectra were collected every 8.1 seconds for up to 10 minutes. A background scan was collected before the beginning of the experiment. The IR was calibrated (wavelength) with polystyrene at the time of use. The TGA was operated under a flow of helium at 90 and 10 cc/min for the purge and balance, respectively. Approximately 14 to 20 mg of sample was loaded into a platinum sample pan and heated from 25° C. to 225° C. at a rate of 20° C./min. The TG instrument was started first, immediately followed by the IR instrument. The calibration standards were nickel and Alumel™. Volatiles were identified from a search of the RH Nicolet TGA Vapor Phase spectral library.

Infrared Spectroscopy (IR)

Infrared spectra were acquired on Magna 860® Fourier transform infrared (FT-IR) spectrophotometer (Nicolet Instrument Corp.) equipped with an Ever-Glo mid/far IR source, an extended range potassium bromide (KBr) beamsplitter, and a deuterated triglycine sulfate (DTGS) detector. A Spectra-Tech, Inc. diffuse reflectance accessory (the Collector™) was used for sampling. Each spectrum represents 128 co-added scans at a spectral resolution of 4 $cm^{-1}$. Sample preparation for the drug substance consisted of placing the sample into a 13-mm diameter cup and leveling the material with a frosted glass slide. A background data set was acquired with an alignment mirror in place. The spectra represent a ratio of the sample single beam data set to the background single beam data set. The spectrophotometer was calibrated (wavelength) with polystyrene at the time of use.

Raman Spectra

Raman spectra were acquired on a Nicolet FT-Raman 960 spectrometer. This spectrometer uses an excitation wavelength of 1064 nm. Approximately 0.5 W of Nd:YVO$_4$ laser power was used to irradiate the samples. The Raman spectra were measured with an indium gallium arsenide (InGaAs) detector. The samples were prepared for analysis by packing them in an NMR tube. The NMR tube was placed in a gold-coated NMR tube holder. Each spectrum is the result of 128 co-added scans acquired at 4 $cm^{-1}$ solution and an autogain setting. The spectrometer was calibrated (wavelength) with sulfur and cyclohexane at the time of use.

$^1$H NMR Spectra

A solution $^1$H NMR spectrum was acquired at ambient temperature on a Bruker Instruments AM-250 spectrometer at a magnetic field strength of 5.87 Tesla ($^1$H Larmor frequency=250 MHz). The sample (5.9 mg) was dissolved in 0.5 mL NMR-grade DMSO-d$_6$. The spectrum was acquired with a $^1$H pulse width of 4 µs, a 5 second delay between scans, a spectral width of 5000 Hz with 8192 data points, and 128 co-added scans. Each free induction decay (FID) was processed with GRAMS/32 AI software v. 6.00 using a Fourier number equal to twice the number of acquired points with an exponential line broadening factor of 0.1 Hz to improve sensitivity. The spectrum was referenced to internal TMS at 0.0 ppm.

Moisture Balance

Moisture sorption/desorption data were collected on a VTI SGA-100 moisture balance system. For sorption isotherms, a sorption range of 5 to 95% relative humidity (RH) and a desorption range of 95 to 5% RH in 10% RH increments were used for analysis. The samples were not dried prior to analysis. Equilibrium criteria used for analysis were less than 0.0100% weight change in 5 minutes with a maximum equilibration time of 3 hours if the weight criterion was not met. Data were not corrected for the initial moisture content of the samples.

Fast Evaporation (FE)

Solutions were prepared in various solvents, the solution was filtered through a 0.2 µm nylon filter. The filtered solution was allowed to evaporate at ambient temperature in an open vial. The solids that formed were isolated and analyzed.

Slow Evaporation (SE)

Solutions were prepared in various solvents and sonicated between aliquot additions to assist in dissolution. Once a mixture reached complete dissolution, as judged by visual observation, the solution was filtered through a 0.2 µm nylon filter. The filtered solution was allowed to evaporate at ambient temperature in a vial covered with aluminum foil perforated with pinholes. The solids that formed were isolated and analyzed.

Slow Cool (SC)

In slow cool experiments, the sample was dissolved with aliquots of a test solvent at an elevated temperature. The resulting solution was rapidly filtered into a vial kept on the same hot plate. Then the vial was capped and the heat source was turned off allowing the hot plate and the vial to cool slowly to ambient temperature. The vial was then allowed to stand at ambient temperature overnight. The presence or absence of solids was noted and if there were no solids present, or the amount of solid judged too small for XRPD analysis, the vial was placed in a refrigerator overnight. Again the presence or absence of solids was noted and, if there were none, the vial was placed in a freezer overnight. Solids were collected by filtration and allowed to dry in the air. If the vial was left open during the slow cool, the technique was referred as slow cool with fast evaporation.

Crash Cool (CC)

In crash cool experiments, the sample was dissolved with aliquots of a test solvent at an elevated temperature. The resulting solution was rapidly filtered into a vial kept on the same hot plate. Then the vial was capped and either immersed in a cooling bath or transferred to a freezer to achieve very rapid cooling of the system from elevated to subzero temperature. Solids were collected by filtration and allowed to dry in the air.

Crash Precipitation (CP)

Crystallization using an antisolvent was also performed either by adding the saturated solution of the drug molecule to relatively large amount of antisolvent or by adding the antisolvent to the saturated solution. In either version, the saturated solution was filtered and the additions were conducted in dropwise manner. If precipitation was not observed, the vial was capped and transferred into a refrigerator. If precipitation occurred, the solids were collected by filtration and allowed to dry in the air under ambient or reduced pressure. These experiments are referred to as crash precipitation at ambient or subambient temperature.

Rotary Evaporation

Solutions were prepared in various solvents. The solution was then filtered into a round bottom flask and the solvent was removed by rotary evaporation. Solids were recovered and analyzed.

Vapor Diffusion

Vapor diffusion precipitation involved placing a vial with a saturated solution of the drug substance into a larger sealed vial containing an antisolvent at ambient temperature. The solids present were recovered by filtration.

Spontaneous Crystallization

Experiments in which crystallization occurred within seconds or minutes of dissolution are referred to as spontaneous crystallization. Solid, from those samples, was collected by filtration under reduced pressure, air-dried, and analyzed.

In order that this invention is more fully understood, the following assays and examples are offered by way of illustration, not limitation.

Assays

IMPDH Activity Inhibition Assay

IMP dehydrogenase activity is assayed following an adaptation of the method first reported by Magasanik. [B. Magasanik et al., *J. Biol. Chem.*, 226, p. 339 (1957), the disclosure of which is herein incorporated by reference]. Enzyme activity is measured spectrophotometrically, by monitoring the increase in absorbance at 340 nm due to the formation of NADH ($\square$340 is 6220 $M^{-1}$ $cm^{-1}$). The reaction mixture contains 0.1 M potassium phosphate 8.0, 0.5 mM EDTA, 2 mM DTT, 200 µM IMP and enzyme (IMPDH human type II) at a concentration of 15 to 50 nM. This solution is incubated at 37° C. for 10 minutes. The reaction is started by adding NAD to a final concentration of 200 µM and the initial rate is measured by following the linear increase in absorbance at 340 nm for 10 minutes. For reading in a standard spectrophotometer (path length 1 cm) the final volume in the cuvette is 1.0 ml. The assay has also been adapted to a 96 well microtiter plate format; in this case the concentrations of all the reagents remain the same and the final volume is decreased to 200 µl. For the analysis of inhibitors, the compound in question is dissolved in DMSO to a final concentration of 20 mM and added to the initial assay mixture for preincubation with the enzyme at a final volume of 2-5% (v/v). The reaction is started by the addition of NAD, and the initial rates measured as above. $K_i$ determinations are made by measuring the initial velocities in the presence of varying amounts of inhibitor and fitting the data using the tight-binding equations of Henderson (Henderson, P. J. F. (1972) Biochem. J. 127, 321).

Cellular Assays

A. Isolation of peripheral blood mononuclear cells (PBMCs): Human venous blood is drawn from normal healthy volunteers using heparin as an anti-coagulant. PBMCs are isolated from blood by centrifugation over Ficoll-paque gradient or CPT tubes (Becton-Dickinson) using standard conditions. PBMCs are harvested, washed and re-suspended in complete RPMI, counted and diluted to $1\times10^6$ cells/mL.

B. PBMC and splenocyte proliferation assays: $5\times10^4$ cells (for human PBMC T cells) or $1\times10^5$ cells (for human PBMC B cells) were added per well of a 96-well plate. For T-cell assays, phyto-hemagglutinin (PHA) is added to a final concentration of 10-20 µg/mL per well for cell. For B-cell assays, Staphylococcal protein A (SPAS) is added to a final concentration of 2 µg/mL per well. Serial 4-fold dilutions of inhibitor stocks is made in complete RPMI media and added to cells such that the final concentration of compounds ranged from 20 µM to 20 nM, while DMSO is maintained at a final concentration of 0.1%. The cells are then incubated for 3 days. All samples are tested in triplicate. Tritiated thymidine (0.4 µCi/well) is added for the last 24 hours of the assay. The cells are harvested onto Betaplate filters and counted in a scintillation counter. Concentrations of compounds required to inhibit proliferation of cells by 50% (IC50 values) are calculated using the SoftMax Pro™ (Molecular Devices) computer software package.

Anti-Viral Assays

The anti-viral efficacy of compounds may be evaluated in various in vitro and in vivo assays. For example, compounds may be tested in in vitro viral replication assays. In vitro assays may employ whole cells or isolated cellular components. In vivo assays include animal models for viral diseases. Examples of such animal models include, but are not limited to, rodent models for HBV or HCV infection, the Woodchuck model for HBV infection, and chimpanzee model for HCV infection.

Abbreviations and terms which are used in the examples that follow and throughout the specification include:
EtOAc: ethyl acetate
i-BuOAc: isobutyl acetate
i-PrOAc: isopropyl acetate
MEK: methyl ethyl ketone
MIBK: methyl isobutyl ketone
TBME: tert-butyl methyl ether
MeOH: methanol
EtOH: ethyl alcohol
TFE: 2,2,2-trifluoroethanol
IPA: isopropyl alcohol
HFIPA: hexafluoroisopropanol
ACN: acetonitrile
THF: tetrahydrofuran
NMP: N-methylpyrrolidinone
DMF: N,N-dimethylformamide
DMSO: dimethylsulfoxide
HCl: hydrochloric acid
$N_2$: nitrogen gas
L: liter
ml: milliliter T$_{max}$ maximum temperature
g: gram
Kg: kilogram
mg: milligram
M: molar
VT: variable temperature
PBMC: peripheral blood mononuclear cells
PHA: phyto-hemagglutinin
SPAS: Staphylococcal protein A
DTT: dithiothreitol
EDTA: ethylenediaminetetraacetic acid
NAD: nicotinamide adenine dinucleotide
CPT: cell preparation tube
RPMI: Roswell Park Memorial Institute
HBV: hepatitis B virus
HCV: hepatitis C virus

EXAMPLES

Example 1

Preparation of Compound 1

Compound 1 used to prepare the polymorphs of this invention may be synthesized using the methods described in the '178 patent. In addition, Compound 1 of this invention may be prepared by standard manipulations of methods known to those skilled in the art

Example 2

Preparation of Form A1 by Recrystallization

Crude Compound 1 was prepared according to the procedure in the '178 patent and isolated by rotary evaporation from ethyl acetate. Form A1 was prepared by recrystallization from crude Compound 1 using the solvents and conditions indicated below in Table 1. For example, approximately 250 mg of Compound 1 was dissolved in 2 ml of methanol at 65° C. The hot solution was allowed to cool rapidly to room temperature. Precipitation occurred while cooling. The precipitate was isolated by filtration, washed with 1 ml of methanol and air-dried under reduced pressure then analyzed by XRPD. The XRPD pattern in each experiment was consistent with Form A1.

TABLE 1

| Expt. # | Description of recrystallization conditions | DSC Events | Form obtained | XRPD analysis |
|---|---|---|---|---|
| 1 | EtOAc/toluene | Sharp endo at 173° C. Broad endo at 186° C. | A | Confirms Form A |
| 2 | crude from EtOAc then recrystallyzed from MeOH | Sharp endo at 174° C. Broad endo at 189° C. | A | Confirms Form A |
| 3 | Recrystallized from n-PrOH, dried in vacuo at 40-45° C. | Endo at 165° C. Broad endo at 184° C. | A | Confirms Form A |
| 4 | Recrystallized from MEK, dried in vacuo at 40-45° C. | Endo at 167° C. Shoulder at 170° C. Broad endo at 183° C. | A | Confirms Form A |
| 5 | Recrystallized from acetone, dried in vacuo at 40-45° C. | Endo at 167° C. Endo at 170° C. Broad endo at 184° C. | A | Confirms Form A |
| 6 | Recrystallized from MiBK, dried in vacuo at 40-45° C. | Endo at 161° C. Endo at 164° C. Broad endo at 180° C. | A | Confirms Form A |
| 7 | Recrystallized from Acetonitrile, dried in vacuo at 40-45° C. | Very broad endo at 89° C. Shoulder at 157° C. Endo at 161° C. Broad endo at 177° C. | A | Confirms Form A |
| 8 | Recrystallized from EtOH, dried in vacuo at 40-45° C. | Endo at 167° C. Shoulder at 170° C. Broad endo at 186° C. | A | Confirms Form A |
| 9 | Recrystallized from MeOH, dried in vacuo at 40-45° C. | Sharp endo at 170° C. Broad endo at 189° C. | A | Confirms Form A |
| 10 | Recrystallized from i-PrOH, dried in vacuo at 40-45° C. | Shoulder at 162° C. Endo at 165° C. Broad endo at 181° C. | A | Confirms Form A |

Abbreviations:
endo = endothermic event.

Example 3

Solubility of Compound 1 at Room Temperature

The solubility of Compound 1 was determined at room temperature in the various solvent and solvent mixtures indicated below in Table 2.

TABLE 2

| Solvent | Solubility mg/mL |
|---|---|
| Acetone | 11 |
| Acetone:H$_2$O 20:80 | <8.9 |
| Acetonitrile | 1.6 |
| 2-Butanone (MEK) | 10.5 |
| EtOH | 1.6 |
| THF | 35 |

Example 4

Solubility of Compound 1 at Elevated Temperatures

The solubility of Compound 1 was determined at elevated temperatures in the various solvents indicated below in Table 3.

TABLE 3

| Solvent | Temperature | Solubility mg/mL |
|---|---|---|
| Acetone | 40° C. | 61 |
|  | Boiling point (56° C.) | 67 |
| MeOH | 50° C. | 36 |
|  | 40° C. | 33 |
|  | Boiling point (65° C.) | 92 |
| t-Butyl methyl ether (MTBE) | 45° C. | <10.4 |
| THF | 40° C. | 75 |
|  | Boiling point (65° C.) | 115 |
| Toluene | 50° C. | <2.3 |

Example 5

Methods to Prepare Form A1 or Amorphous Form

Table 4 below provides a summary of experimental methods carried out on Compound 1 using various solvents, conditions, and experimental techniques. The resulting Form A1 or amorphous form obtained was dried in vacuo then analyzed by XRPD. In each case, XRPD analysis was consistent with the indicated form obtained.

TABLE 4

| Solvent | Method | Observation | Form obtained | XRPD run |
|---|---|---|---|---|
| Acetone | — | — | — | — |
|  | SE | Transparent and glassy | A l.c. | yes |
|  | CC (40° C. to −17° C.) | Tiny crystals | A | yes |
|  | SC (40° C. to RT) & FE | Mainly chunky in irregular shapes and some hexagonal plates and tablets, elongated prismatic crystals | A | yes |
|  | — | — | — | yes |
|  | SC (40° C. to RT) | Off-white solid | A | yes |
|  | SC (40° C. to RT) & FE | Off-white solid; hexagonal plates | A | yes |
|  | SC (56° C. to RT) & FE, then seeded w/ form A | Attempt for single crystal Tiny beads | A | yes |
| Acetone:H$_2$O 20:80 | Slurry, 24 h | — | A | yes |
| MeCN:n-PrOH 80:20 | FE | — | Amorphous | yes |
| 2-Butanone (MEK) | — | — | — | — |
|  | SE | Transparent and glassy | Amorphous | yes |
| EtOH | FE | Transparent and glassy, partially white | Amorphous | yes |
|  | SE | Transparent and glassy | — | — |
| MeOH | Slurry, 48 h | — | A | yes |
|  | CC (40° C. to −84° C.), 3 h Equilibrated at RT | Clear solution, Needles, blades in rosettes | A | yes |
|  | SC (40° C. to RT) & FE | — | Amorphous | yes |
|  | CC (65° C. to −84° C.), 1 h | Chunky crystals | A | yes |

TABLE 4-continued

| Solvent | Method | Observation | Form obtained | XRPD run |
|---|---|---|---|---|
| | VD in H$_2$O | Needles, blades, rosettes | A | yes |
| MTBE | Slurry at 45° C., 2 h | — | A | yes |
| THF | CP with toluene | Clear solution | — | — |
| | CC (40° C. to −84° C.), 3 h Stored at −17° C. Equilibrated at RT, consecutive FE | Precipitation occurred in insignificant amount. After FE: transparent and glassy (ref.: 859-32, 36) | Amorphous | yes |
| | — | — | — | — |
| | CP in cold H$_2$O Slurry, 0.5 h | — | A | yes |
| THF:Toluene 15:85 | FE | Fine white powder, Chunky crystals | A | yes |
| Toluene | Slurry at 50° C., 24 h | — | A | yes |
| Acetone | | | | |

Abbreviations:
CC = crash cool;
CP = crash precipitation;
FE = fast evaporation;
SC = slow cool;
SE = slow evaporation;
VD = vapor diffusion;
h = hour;
RT = room temperature
Abbreviations:
l.c. = low crystallinity;

Example 6

Preparation of Form B2 by Slow Cool with Concurrent Fast Evaporation

A slow cool experiment was conducted from a warm methanol (approximately 50° C.) solution with concurrent fast evaporation. For example, approximately 500 mg of Compound 1 was dissolved in 14 ml of methanol at 50° C. The hot solution was filtered, allowed to slowly cool to room temperature, evaporated to dryness and then analyzed by XRPD. The XRPD pattern was consistent with Form B2.

Example 7

Preparation of Form A1 From Form B2

Form B2 recrystallized spontaneously from methanol and acetone affording Form A1. The solid obtained was filtered, dried in vacuo, then analyzed by XRPD. The XRPD pattern was consistent with Form A1.

We claim:

1. A polymorphic Form B2 of (S)-1-cyanobutan-2-yl (S)-1-(3-(3-(3-methoxy-4-(oxazol-5-yl)phenyl)ureido)phenyl)ethylcarbamate.

2. The polymorphic Form B2 according to claim 1, wherein the polymorph has a peak position at about 4.1 degrees 2-theta in an x-ray powder diffraction pattern obtained using Cu K alpha radiation.

3. A polymorphic Form B2 of (S)-1-cyanobutan-2-yl (S)-1-(3-(3-(3-methoxy-4-(oxazol-5-yl)phenyl)ureido)phenyl)ethylcarbamate, wherein said polymorphic Form B2 is characterized by peak positions at about 4.1, 12.6, 14.4, 16.4, 22.1, or 27.1 degrees 2-theta in an x-ray powder diffraction pattern obtained using Cu K alpha radiation.

4. A polymorphic Form B2 of (S)-1-cyanobutan-2-yl (S)-1-(3-(3-(3-methoxy-4-(oxazol-5-yl)phenyl)ureido)phenyl)ethylcarbamate, wherein said polymorphic Form B2 has a peak position at about 4.1 degrees 2-theta in an x-ray powder diffraction pattern obtained using Cu K alpha radiation.

5. A polymorphic Form B2 of (S)-1-cyanobutan-2-yl (S)-1-(3-(3-(3-methoxy-4-(oxazol-5-yl)phenyl)ureido)phenyl)ethylcarbamate, wherein said polymorphic Form B2 has a peak position at about 12.6 degrees 2-theta in an x-ray powder diffraction pattern obtained using Cu K alpha radiation.

6. A polymorphic Form B2 of (S)-1-cyanobutan-2-yl (S)-1-(3-(3-(3-methoxy-4-(oxazol-5-yl)phenyl)ureido)phenyl)ethylcarbamate, wherein said polymorphic Form B2 has a peak position at about 14.4 degrees 2-theta in an x-ray powder diffraction pattern obtained using Cu K alpha radiation.

7. A polymorphic Form B2 of (S)-1-cyanobutan-2-yl (S)-1-(3-(3-(3-methoxy-4-(oxazol-5-yl)phenyl)ureido)phenyl)ethylcarbamate, wherein said polymorphic Form B2 has a peak position at about 16.4 degrees 2-theta in an x-ray powder diffraction pattern obtained using Cu K alpha radiation.

8. A polymorphic Form B2 of (S)-1-cyanobutan-2-yl (S)-1-(3-(3-(3-methoxy-4-(oxazol-5-yl)phenyl)ureido)phenyl)ethylcarbamate, wherein said polymorphic Form B2 has a peak position at about 22.1 degrees 2-theta in an x-ray powder diffraction pattern obtained using Cu K alpha radiation.

9. A polymorphic Form B2 of (S)-1-cyanobutan-2-yl (S)-1-(3-(3-(3-methoxy-4-(oxazol-5-yl)phenyl)ureido)phenyl)ethylcarbamate, wherein said polymorphic Form B2 has a peak position at about 27.1 degrees 2-theta in an x-ray powder diffraction pattern obtained using Cu K alpha radiation.

Figure 2:
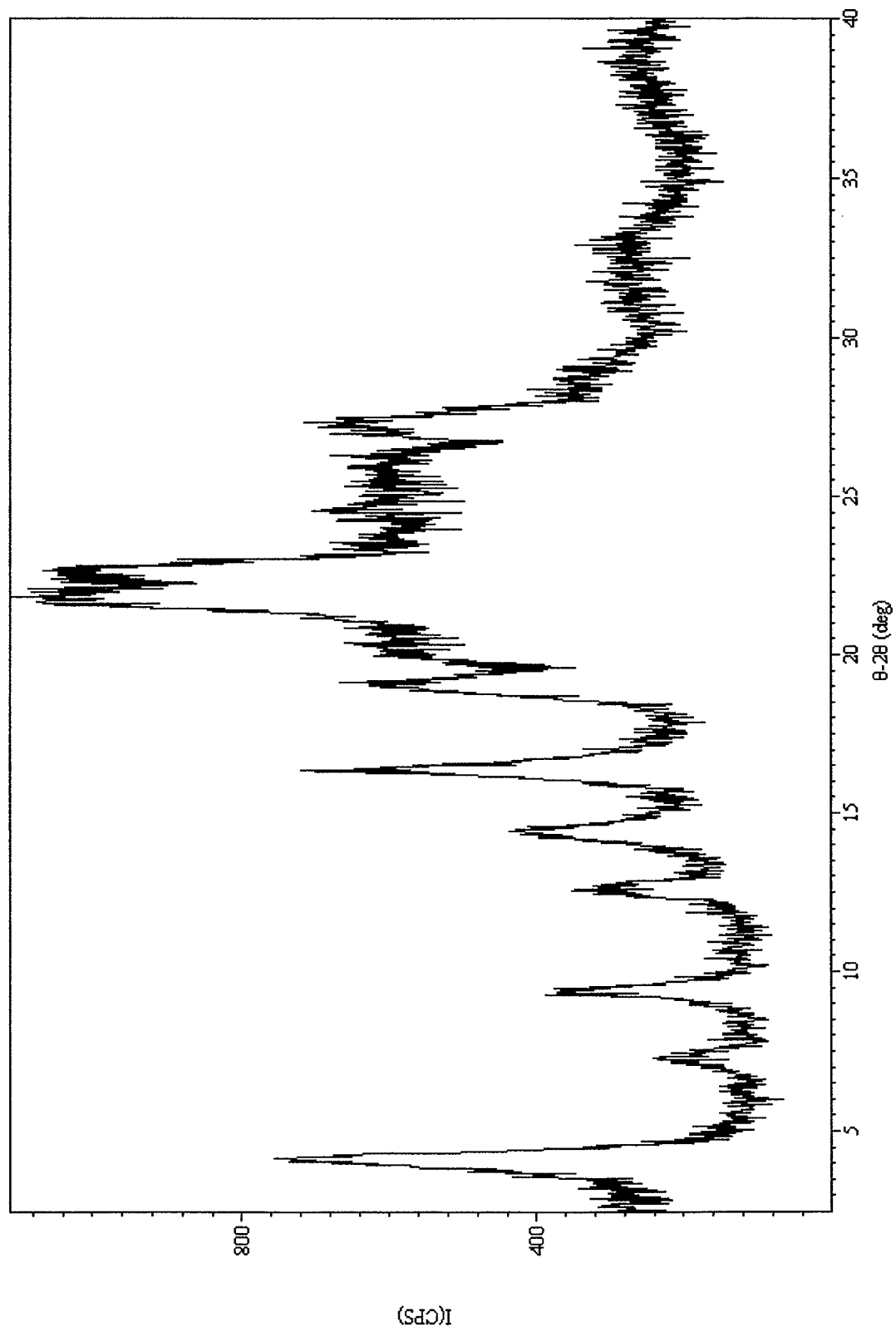
FIG. 2 is an XRPD of Form B2 of (S)-1-cyanobutan-2-yl (S)-1-(3-(3-(3-methoxy-4-(oxazol-5-yl)phenyl)ureido)phenyl)ethylcarbamate.
Figure 3:
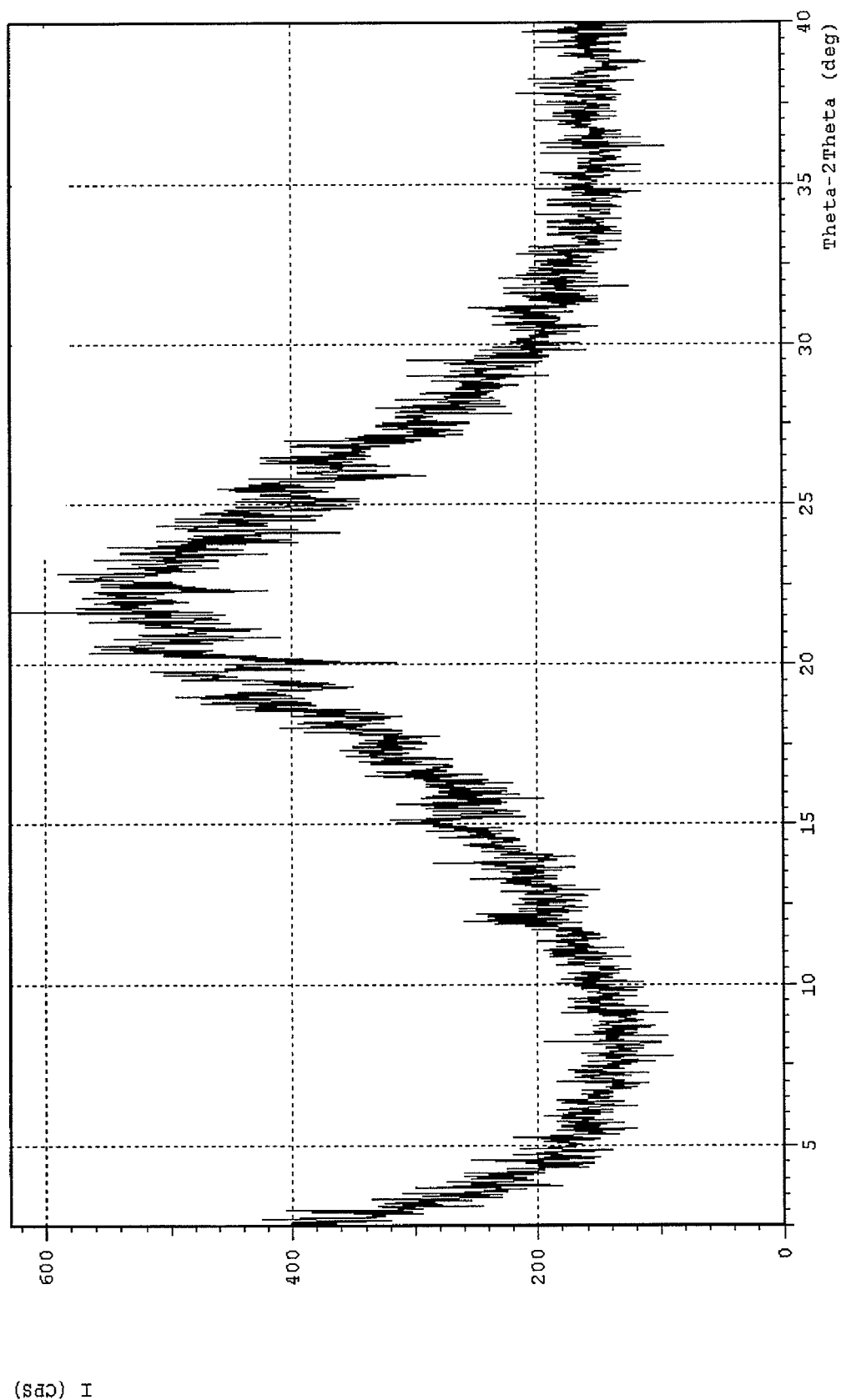
FIG. 3 is an XRPD of amorphous form of (S)-1-cyanobutan-2-yl (S)-1-(3-(3-(3-methoxy-4-(oxazol-5-yl)phenyl)ureido)phenyl)ethylcarbamate.
Figure 4:
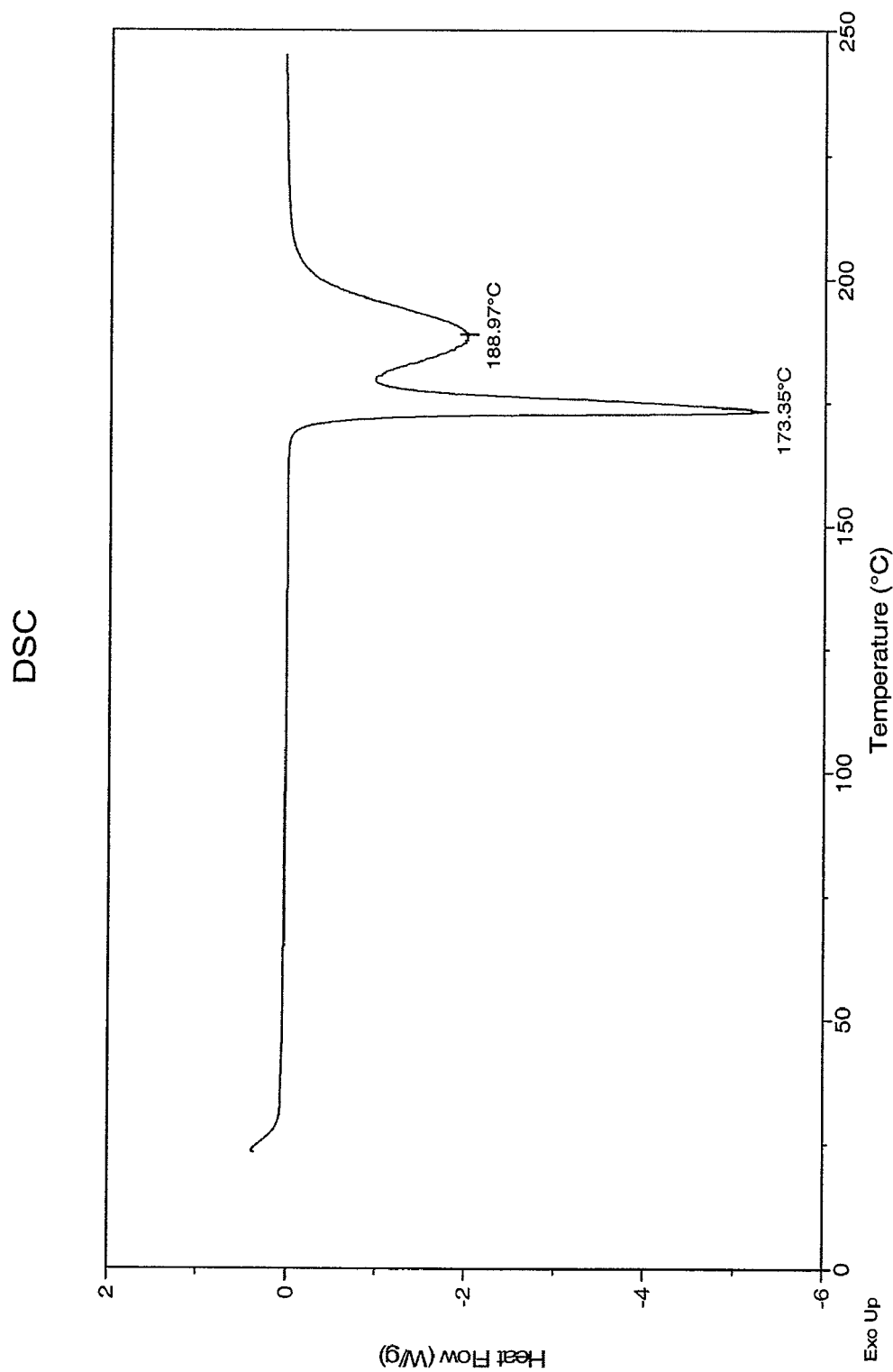
FIG. 4 is a Differential Scanning Calorimetry (DSC) thermogram of Form A1 of (S)-1-cyanobutan-2-yl (S)-1-(3-(3-(3-methoxy-4-(oxazol-5-yl)phenyl)ureido)phenyl)ethylcarbamate.
Figure 5:
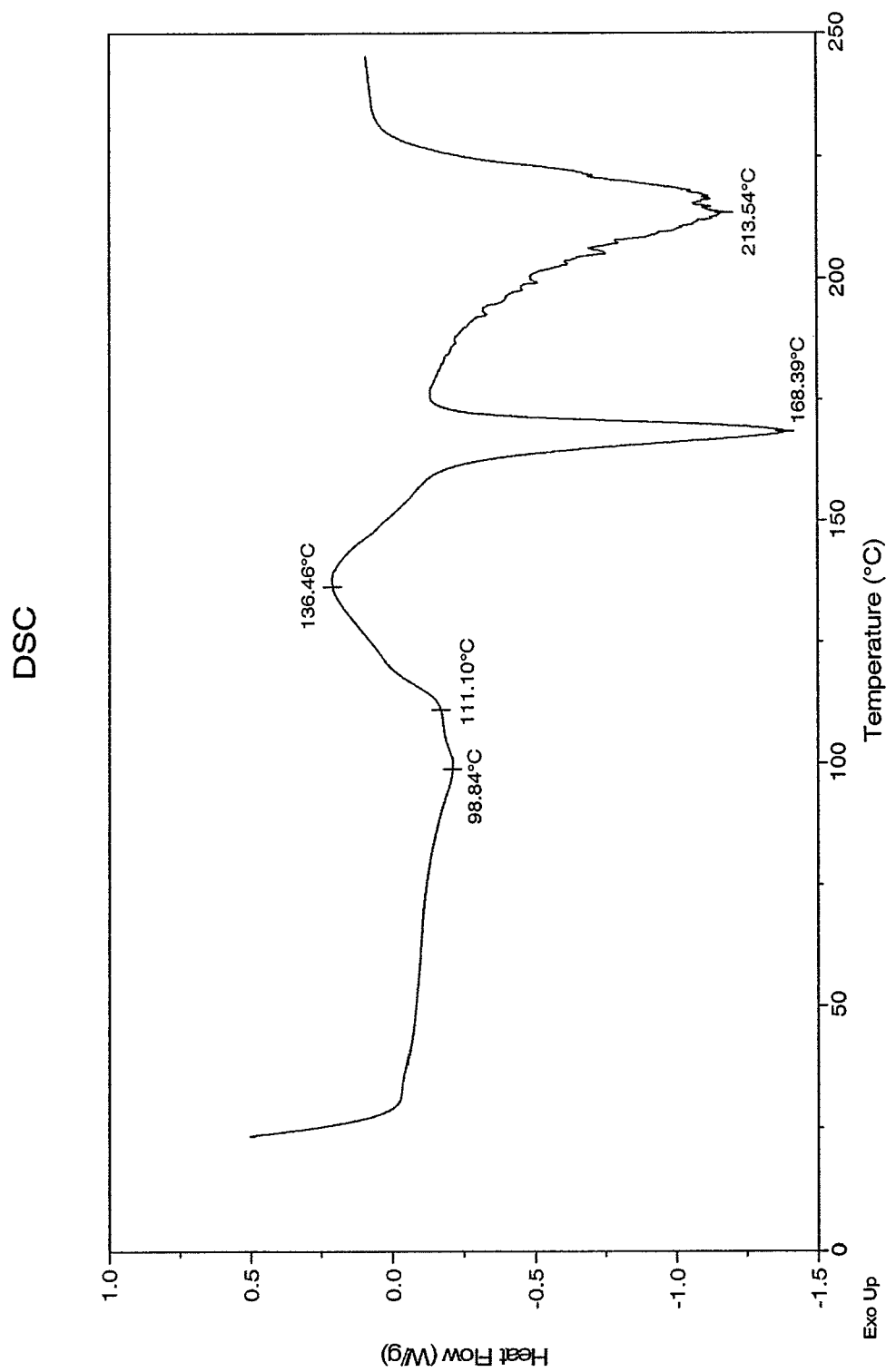
FIG. 5 is a DSC thermogram of amorphous (S)-1-cyanobutan-2-yl (S)-1-(3-(3-(3-methoxy-4-(oxazol-5-yl)phenyl)ureido)phenyl)ethylcarbamate.

10. A polymorphic Form B2 of (S)-1-cyanobutan-2-yl (S)-1-(3-(3-(3-methoxy-4-(oxazol-5-yl)phenyl)ureido)phenyl)ethylcarbamate, wherein said polymorphic Form B2 is characterized by an x-ray powder diffraction pattern as shown in FIG. 2.

* * * * *